(12) United States Patent
Uenishi

(10) Patent No.: US 6,505,625 B1
(45) Date of Patent: Jan. 14, 2003

(54) MOUTHPIECE

(76) Inventor: Masakazu Uenishi, 81, Minami-chugen-machi, Wakayama-shi, Wakayama (JP), 640-8251

( * ) Notice: Subject to any disclaimer, the term of this patent is extended or adjusted under 35 U.S.C. 154(b) by 0 days.

(21) Appl. No.: 09/937,478

(22) PCT Filed: Mar. 26, 1999

(86) PCT No.: PCT/JP99/01593
§ 371 (c)(1),
(2), (4) Date: Sep. 26, 2001

(87) PCT Pub. No.: WO00/57808
PCT Pub. Date: Oct. 5, 2000

(51) Int. Cl.⁷ .................................................. A61F 5/56
(52) U.S. Cl. ...................... 128/848; 128/859; 602/902
(58) Field of Search ................................ 128/846, 848, 128/859–862; 602/902; 433/6

(56) References Cited

U.S. PATENT DOCUMENTS

| 4,376,628 A | | 3/1983 | Gaba | |
| 4,505,672 A | | 3/1985 | Kurz | |
| 4,898,535 A | | 2/1990 | Bergersen | |
| 5,313,960 A | * | 5/1994 | Tomasi | 128/848 |
| 5,499,633 A | * | 3/1996 | Fenton | 128/848 |
| 5,823,193 A | * | 10/1998 | Singer | 128/848 |
| 6,055,986 A | * | 5/2000 | Meade | 128/848 |

FOREIGN PATENT DOCUMENTS

| EP | 28237 | 5/1981 |
| EP | 337201 | 10/1989 |
| JP | 3-21235 | 1/1991 |
| JP | 11-155884 | 6/1999 |
| NL | 7903648 | 5/1979 |
| WO | 80/02368 | 11/1980 |

* cited by examiner

*Primary Examiner*—Michael A. Brown
(74) *Attorney, Agent, or Firm*—Wenderoth, Lind & Ponack, L.L.P.

(57) ABSTRACT

A mouthpiece has a simple structure, and is therefore easy to machine for adjustment, and is extremely inexpensive. The mouthpiece has an upper piece to be fitted to the upper jaw dentition, and a lower piece vertically opposed to the upper piece and to be fitted to the lower jaw dentition. Projections are provided on the opposed surface of one of the upper and lower pieces and project toward the other piece, and a supporting surface is provided on the other piece for supporting the projections when it comes in contact therewith. An upper dentition fitting groove for fitting the upper piece to the upper-jaw dentition is formed in the upper surface of the upper piece, and a lower dentition fitting groove for fitting the lower piece to the lower-jaw dentition is formed in the lower surface of the lower piece.

15 Claims, 11 Drawing Sheets

MOUTHPIECE

TECHNICAL FIELD

The present invention relates to a mouthpiece used to equally stretch right and left side lower jaw supporting muscles thereof with a bite raising device, so as to correct one's posture.

BACKGROUND ART

General bone structure of and around the upper and lower jaws is illustrated in FIGS. 17(a) and 17(b).

An occlusion of rows of teeth when the upper and lower jaws are closed is shown in FIG. 17(a). In FIG. 17(a), the skull supported on the first cervical vertebrae 25 at the top end of the spine and the upper row of teeth 22 arranged in the upper jaw 20 of a front part of the skull are shown. The lower jaw 21 having the row of teeth 23 on the lower jaw side is supported in a complex fashion by various muscles including a masseteric muscle. One naturally takes a posture where one's head can be kept at a state in which the occlusion plane indicated by an axis X is aligned with an ideal occlusion plane (an approximately level plane). It is desirable that an axis Y perpendicular to the axis X extends along a vertical line.

It is known that the lower jaw 21 moves vertically around and further swings back and forth and side to side in a three-dimensional manner around a median atlantoaxial joint $T_0$ between the first cervical vertebrae 25 and the second cervical vertebrae 26, and not around a point J of a temporomandibular joint 24, as shown in FIG. 17(b).

When occlusion surfaces of the teeth wear with age, for example, so that the vertical occlusal height of the opposing upper and lower rows of teeth decreases, or "the dental bite goes low", as a whole, the upper jaw 20 tries to meet the lower jaw 21 and, as a result, the head leans forward. This causes the first cervical vertebrae 25 and the second cervical vertebrae 26 to move, forward away from their ideal positions, so that they come into a straight bar-like form. Along with the cervical vertebrae becoming out of position, the entire spinal cord is caused to hunch, leading to a possible hunchback and further causing a possible lower back problem.

On the other hand, when the vertical occlusal height is decreased at either lateral end due to a significant partial bite, improper dental care after extraction of a tooth, or excessive grinding of a carious tooth, in other words, when an axis Z perpendicular to the both axes of X and Y (a horizontally extending axis, not shown) is slanted, muscle spindles of the lower mandibular raising muscles of the lower jaw are loosened. This information is transmitted to the brain through trigeminal nerves, and gives a strong stress to the brain. In response to the information, the brain automatically signals central orders to shorten the muscle spindles. Based on the orders, the mandibular raising muscles of the lower jaw at rest are reset to be shorter and also the entire skeletal muscles of the body on the same side are reset to be shorter. These orders are issued day and night, so that the brain and muscles fatigue chronically, then causing possible deterioration of the function of the brain and body.

Then, the neck is slanted to a lower vertical occlusal height, while on the other hand, the muscles of the shoulder on the opposite side increase in tension, in order to try to prevent the slant of the neck. It is known that this muscular contraction and tension puts the vertebral artery and vertebral nerve under stress, and induce discomfort complaints, such as stiffness of shoulder, vertigo, buzzing, headache, tinnitus and visceral disturbance, and autonomic imbalance.

To improve the partial muscular stretch and tension caused by the lowering of the vertical occlusal height could result in the alleviation of disease caused by deterioration of the function of the brain and improve the athletic talents typified by one's reflexes and dexterity, of physical capabilities typified by muscle strength and muscular balance of the entire body, and of learning ability, thinking ability and concentration power.

To this end, it is observed that a weightlifter having a horizontally deviated vertical occlusal height lifts a weight in a state in which the weightlifter's lower vertical occlusal height end is inclined downward. In the U.S., it is compulsory for American to have bite raising mouthpieces on during the game, in order to prevent a disability caused by the muscular tension.

There has been proposed a mouthpiece used to straighten one's back to correct the one's posture, as disclosed by Japanese Utility Model Publication No. Sho 62-14833.

This proposed mouthpiece is designed to be fitted to either the row of teeth at the upper jaw side or the row of teeth at the lower jaw side. It comprises a first tooth row fitting piece to be fitted to the row of teeth located on one side from the median line, a second tooth row fitting piece to be fitted to the row of teeth located on the other side from the median line, and an arcuate connecting portion for connecting the pair of tooth row fitting pieces. In this mouthpiece, a plane perpendicular to a tooth axis of an opposing tooth (a shearing drag surface) is formed on a supporting surface of each of the tooth row fitting pieces by grinding for each opposing tooth.

In the mouthpiece disclosed by the publication above, it is necessary to grind and polish the shearing drag surface in a skillful manner in agreement with a teeth alignment on the non-fitting side, a moving range of intercuspal occlusal position on the lingual side and a vertical occlusal height. For example, the shearing drag surface must be adjusted for fit to each of the four back teeth at opposite ends of the rows of teeth and, besides, since the lower jaw must be moved so smoothly that one cannot feel any stress, a considerable skillfulness is required for the adjustment. It takes about 1–2 hours to do the dental treatment for each adjustment for fit. Thus, the prior art has the problems in that it fails to consider the labor of the dentist, and the medical and technical service fees which are expensive.

In light of the above-noted problems of the prior art, the present invention has been made. It is an object of the present invention to provide a mouthpiece of a simplified structure to facilitate an adjustment process for dental fit and significantly lower in price.

SUMMARY OF THE INVENTION

To accomplish the object mentioned above, a mouthpiece according to the present invention comprises an upper piece to be fitted to a row of teeth on an upper jaw side and a lower piece to be fitted to a row of teeth on a lower jaw side used in a vertically confronting relation with the upper piece, wherein one of an opposing surface of the upper piece and an opposing surface of the lower piece has at least two projections projecting toward the other piece and the other opposing surface has a supporting surface formed to support the at least two projections in abutment relation with them.

Each of the projections comprises a projecting piece formed separately from the one opposing surface and movable toward the other piece, projection height adjusting means for guiding the projecting piece toward the other piece to vary a height of the projection from the one opposing surface to a tip of the projecting piece, and projecting piece fixing means for fixing the projecting piece to the one opposing surface at a height of the projection set by the projection height adjusting means.

In the constitution mentioned above, the projection height adjusting means comprises a first sliding surface formed on the projecting piece and a second sliding surface formed on the one opposing surface to slide over the first sliding surface of the projecting piece, so as to guide the projecting piece toward the other piece.

Further, in the constitution mentioned above, the projection height adjusting means and the projecting piece fixing means comprise a first threaded portion provided on the projecting piece and a second threaded portion provided on the one opposing surface to be threadedly engaged with the first threaded portion of the projecting piece, respectively.

In any of the constitutions mentioned above, an upper tooth row fitting groove to be fitted to the row of teeth on the upper jaw side is formed on a top surface of the upper piece and a lower tooth row fitting groove to be fitted to the row of teeth on the lower jaw side is formed on a bottom surface of the lower piece, the upper piece and the lower piece being supported to the row of teeth on the upper jaw side and the row of teeth on the lower jaw side, respectively, via soft lining material filled in the upper tooth row fitting groove and the lower tooth row fitting groove.

DETAILED DESCRIPTION OF THE INVENTION

In the following, preferred embodiments of the present invention will be described with reference to the accompanying drawings.

Figure 1:
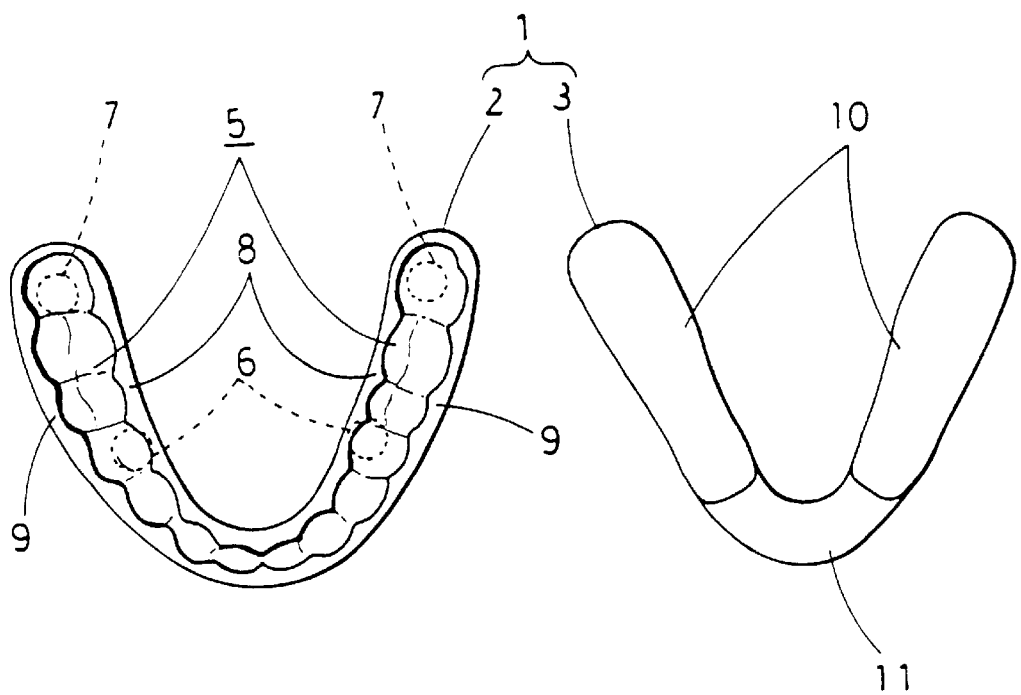
FIG. 1 is a plan view of a mouthpiece according to one embodiment of the invention.
Figure 2:
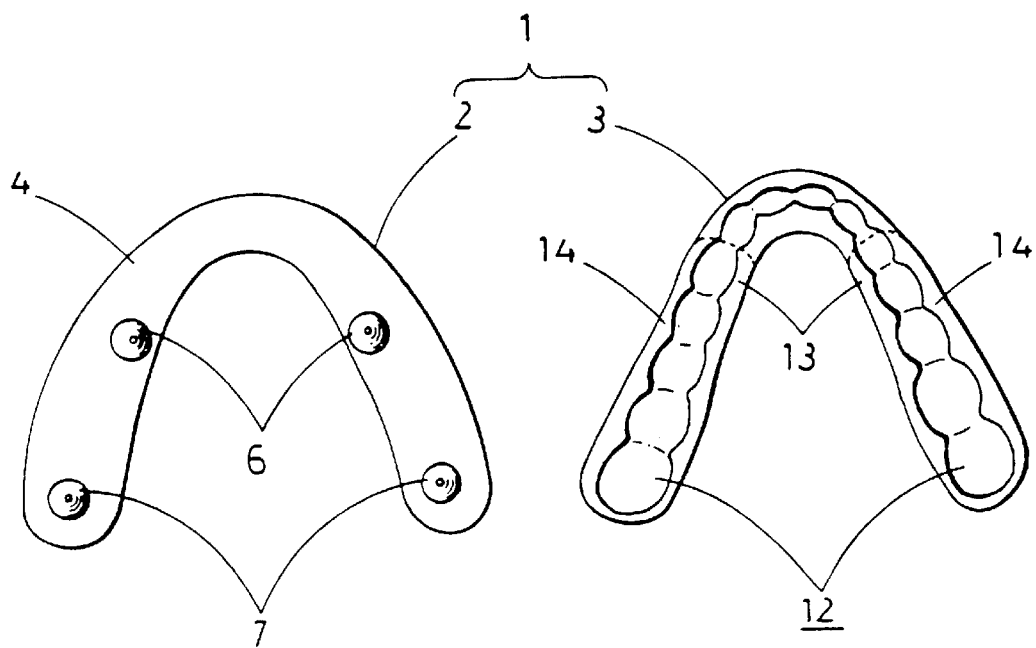
FIG. 2 is a bottom view of the mouthpiece of FIG. 1.
Figure 3:
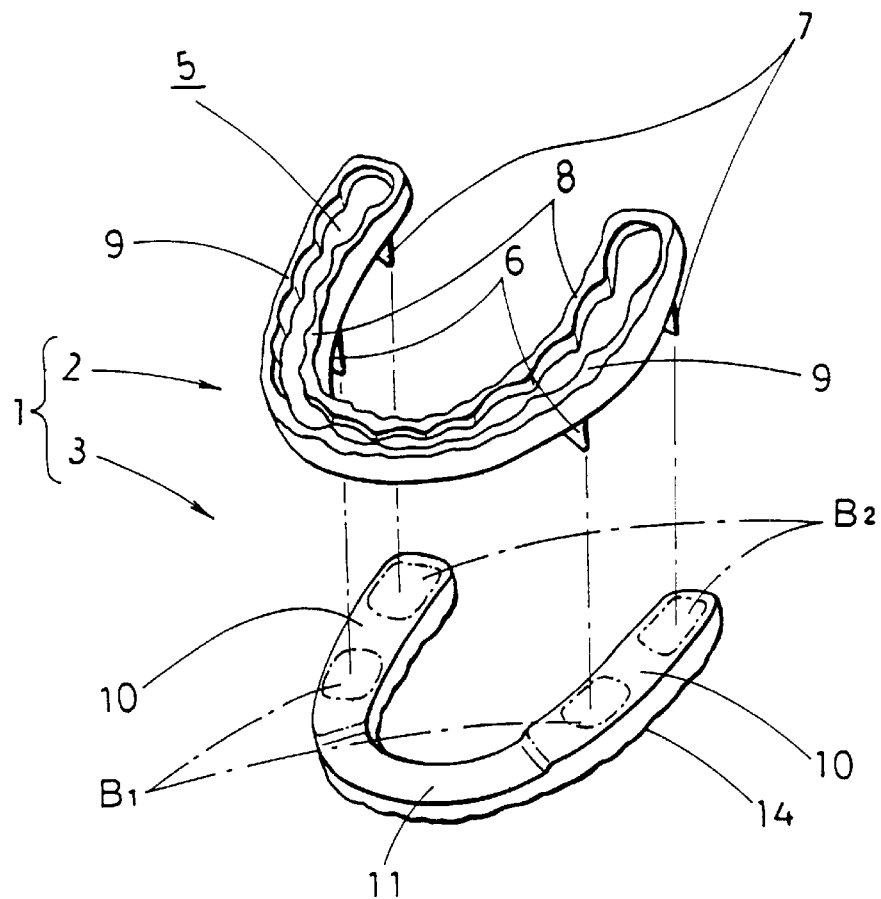
FIG. 3 is a perspective view of the mouthpiece of FIG. 1.
Figure 4:
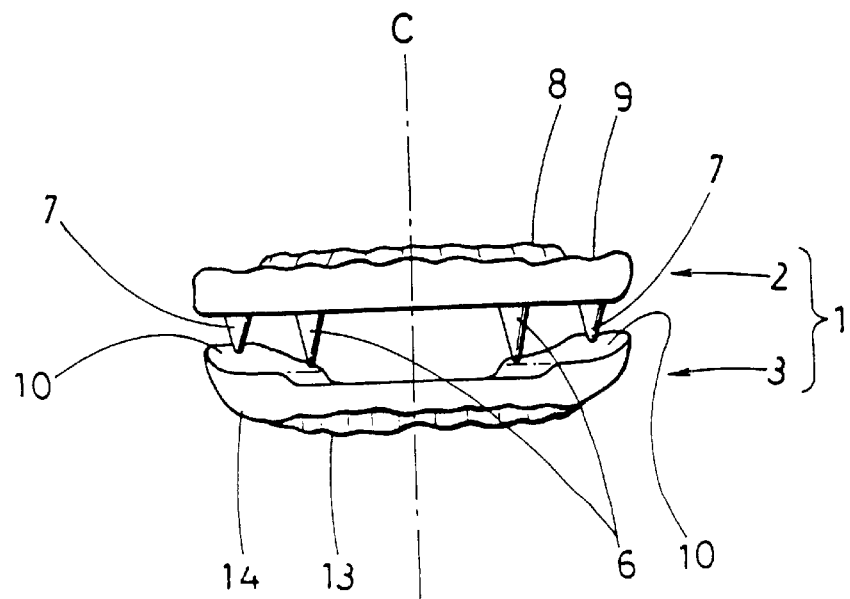
FIG. 4 is a front view of the mouthpiece of FIG. 1.

FIG. 1 is a plan view of a mouthpiece according to one embodiment of the invention, FIG. 2 is a bottom view of the mouthpiece, FIG. 3 is a perspective view of the mouthpiece, and FIG. 4 is a front view of the mouthpiece.

In the respective diagrams, the mouthpiece 1 of this embodiment comprises a combination of an upper piece 2 to be fitted to a row of teeth on an upper jaw side and a lower piece 3 to be fitted to a row of teeth on a lower jaw side used in a vertically confronting relation with the upper piece 2. The upper piece 2 and the lower piece 3 are made, for example, of methyl methacrylate resin for dental use and are formed into a general horseshoe arch form to fit to all upper and lower teeth, when viewed from the top.

The upper piece 2 has, on its opposing surface (bottom surface) 4, four conical projections 6, 6, 7, 7 projecting therefrom toward the lower piece 3. The upper piece 2 has, in its top surface, an upper tooth row fitting groove 5 surrounded by its inner and outer edges 8 and 9.

The lower piece 3 has, on its opposing surface, supporting surfaces 10, 10 for resting and supporting the projections 6, 6, 7, 7 thereon. The lower piece 3 has, in its bottom surface, a lower tooth row fitting groove 12 surrounded by its inner and outer edges 13 and 14.

The supporting surfaces 10, 10 of the lower piece 3 are integrally connected to each other through a depressed thin sheet portion 11. Processed surfaces $B_1$, $B_2$ to be subjected to the cutting out of adequate shearing drag surfaces for the projections 6, 6, 7, 7 are set on the supporting surfaces 10, 10 at locations thereof at which the projections 6, 6, 7, 7 are put in abutment with the supporting surfaces. Reference mark C in FIG. 4 represents a current body axis or median line of a patient.

Sequentially, the fitting and adjusting order of the mouthpiece 1 will be described.

Figure 5A:
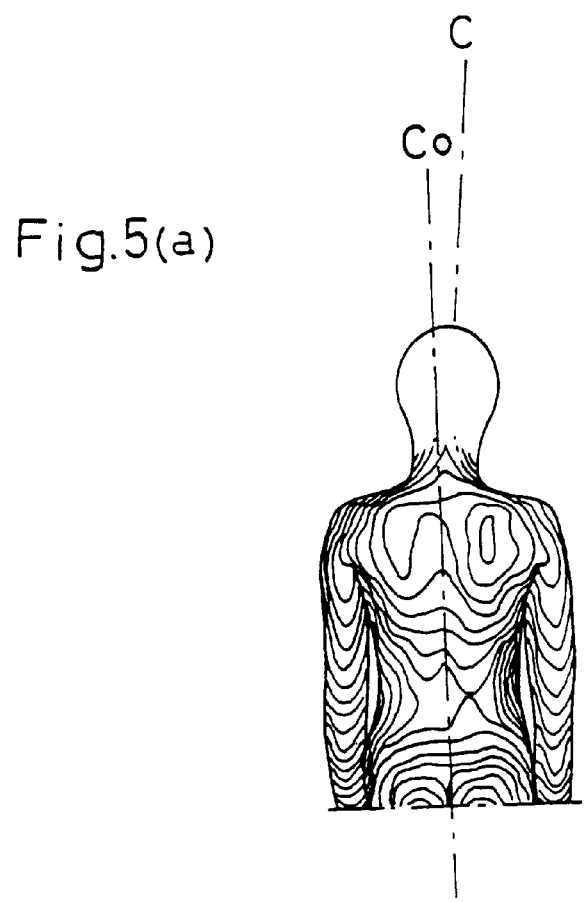
FIGS. 5(a) and (b) illustrate the back of a patient fitting the mouthpiece on as taken by a moiré topography with FIG. 5(a) being an illustration showing the state of the back of the patient before fitting the mouthpiece, and FIG. 5(b) being an illustration showing the state of the back of the patient after using the mouthpiece for about 1 month.

First, a photograph of the back of the patient before fitting the mouthpiece on is taken by moiré topography, as shown in FIG. 5(a). The result of the moiré topography showing the undulation of the body surface in contour lines shows that the present body axis C of this patient is slanted to the right with respect to an ideal body axis $C_0$. This indicates that the vertical occlusal height on the right-hand side is lower than that on the left-hand side. Then, the dentist checks the body axis C with reference to the photograph of the moiré topography, to make the patient's posture change, so as to bring the body axis C into coincidence with the ideal body axis $C_0$ (vertical line). Based on the variation of the patient's posture on the right and left sides thereof, a required quantity of bite raising of the vertical occlusal height on the right and left sides is determined. In addition, the patient's back and forth posture is visually observed from the side of the body, for using it as part of the reference material for determination of a total quantity of bite raising of the vertical occlusal height on the two rows of teeth.

Figure 6:
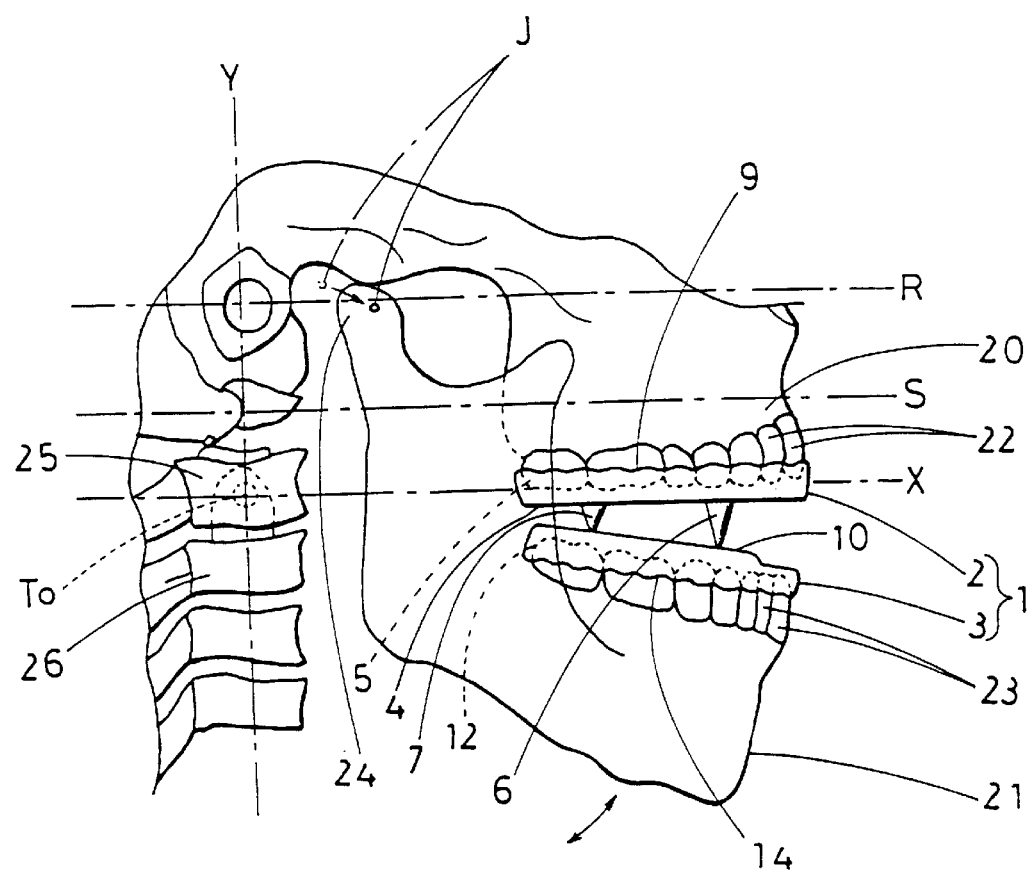
FIG. 6 is an illustration of the state in which the mouthpieces are fitted to the upper and lower rows of teeth when viewed from a side elevation.

Then, the patient's head is kept in the state in which the axis X indicating the occlusion plane of the row of teeth 22 on the upper jaw side is in a substantially horizontal position, as shown in FIG. 6. In this state, the upper tooth row fitting groove 5 is formed to snugly fit to the row of teeth 22 on the upper jaw side so that the opposing surface 4 of the upper piece 2 is in parallel to a nasoauditory meatus R connecting between a subnasal position and a lughole or a HIP plane S (a hamular-notch-incisal-papilla plane) connecting between an incisive papilla at the back of anterior tooth and right and left hamular notches at the back of the molars. On the other hand, the lower tooth row fitting groove 12 is formed to snugly fit to the row of teeth 23 on the lower jaw side so that the occlusion plane of the row of teeth 23 on the lower jaw side is in substantially parallel to the supporting surfaces 10.

A group of muscles supporting the lower jaw 21 have memorized their mandibular movement in accordance with the horizontal difference in vertical occlusal height so far. So, when the patient fits the mouthpiece 1 at this time on, there appears inconformity in vertival occlusal height between the right and left sides. Then, the patient moves the lower jaw 21 so that the lip can be made bilaterally symmetrical, and the center line at the time is determined as the median line C (See FIG. 4).

Then, the projections 6, 7 are adjusted in length so that they can all be brought into contact with the supporting surfaces 10 simultaneously when the lower jaw 21 is opened at a predetermined angle corresponding to a required quantity of bite raising of the vertical occlusal height and also the mouthpiece 1 is occluded in the state in which the median line C is determined.

Then, the adjustment of the shearing drag surface on the supporting surfaces 10 will be described. In general, the adjustment of the shearing drag surface is performed in parallel with the adjustment of the length of the projections 6, 7, to have a good balance therebetween. For facilitation of understanding of the present invention, the description thereon will be given here separately.

First, consideration will be taken on a lateral movement path in the condition in which the projections 6, 7 of the upper piece 2 are all in contact with the supporting surfaces 10 of the lower piece 3. Here, the shearing drag surfaces perpendicular to the tooth axes of the opposing teeth are formed on the processed surfaces $B_1$, $B_2$ at locations thereof to abut with the projections 6, 7.

The shearing drag surfaces are cut out one by one from the molar side to the premolar side for each separate projection 6, 7. If the adjoining shearing drag surfaces are not aligned with each other, in other words, if the adjoining shearing drag surfaces are different in inclination, then the boundaries between the both shearing drag surfaces are allowed to gently vary in inclination.

Figure 7A:
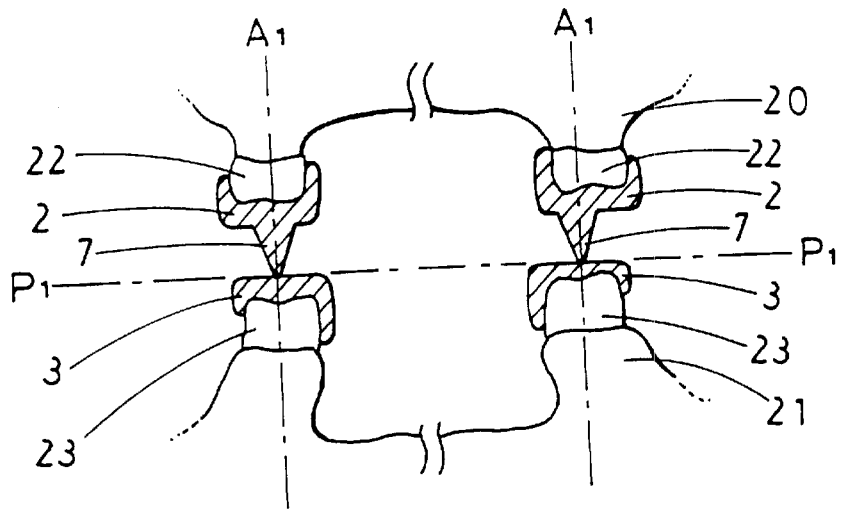
FIGS. 7(a) to (c) illustrate in section inclination, a shearing drag surface formed on a top surface of a lower piece of the mouthpiece by processing, with FIG. 7(a) being an illustration of a type 1 occlusion, FIG. 7(b) being an illustration of a type 2 occlusion, and FIG. 7(c) being an illustration of a type 3 occlusion.

To this end, in the type 1 occlusion wherein the lower jaw 21 and the upper jaw 20 are generally identical in size, shearing drag surfaces $P_1$, $P_1$ perpendicular to tooth axes $A_1$, $A_1$ connecting between the teeth on the upper jaw side and the teeth on the lower jaw side are often formed, as shown in FIG. 7(a). In this type 1 occlusion, since the supporting surfaces ($P_1$, $P_1$) which are originally level with each other and in one plane can be used as reference planes, the adjustment in length of the projections 6, 7 and the adjustment in inclination of the shearing drag surfaces can be made with comparative ease.

Figure 7B:
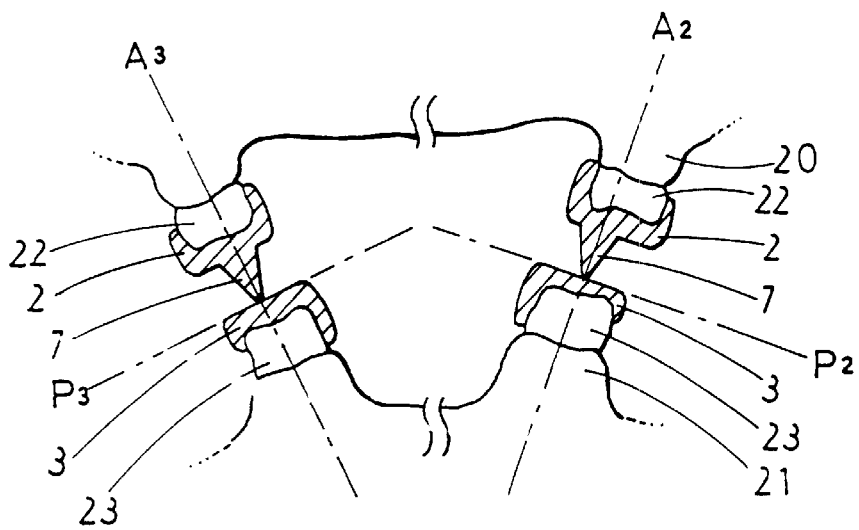

In the type 2 occlusion wherein the lower jaw 21 is smaller than the upper jaw 20, a shearing drag surface $P_2$ perpendicular to a tooth axis $A_2$ and a shearing drag surface $P_3$ perpendicular to a tooth axis $A_3$ are often formed, as shown in FIG. 7(b).

Figure 7C:
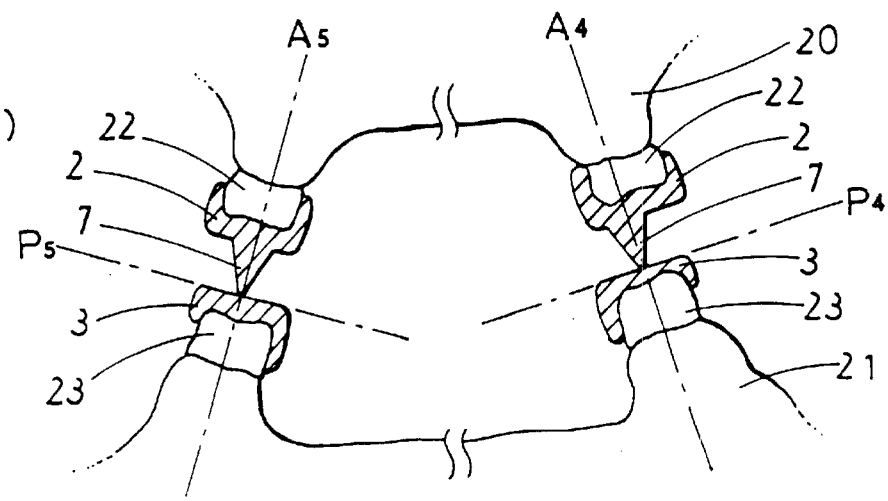

In the type 3 occlusion wherein the lower jaw 21 is larger than the upper jaw 20, a shearing drag surface $P_4$ perpendicular to a tooth axis $A_4$ and a shearing drag surface $P_5$ perpendicular to a tooth axis $A_5$ are often formed, as shown in FIG. 7(c).

For the patient of the occlusion corresponding to the type 2 occlusion or the type 3 occlusion (See FIG. 7(b) or FIG. 7(c)), an alternative may be taken wherein the opposing surfaces of the upper and lower pieces are formed into level planes, like the shearing drag surfaces $P_1$, $P_1$, respectively, and also are widened laterally, and further the projections 6, 7 are formed to extend along the vertical axis, like the tooth axes of $A_1$. This enables the adjustment in length of the projections 6, 7 and the adjustment in inclination of the shearing drag surfaces $P_2$–$P_5$ to be made with ease, as is the case with the mouthpiece easy for adjustment for the type 1 occlusion (See FIG. 7(a)).

The patient is prompted to fit the mouthpiece 1 thus adjusted for about one week. After the fitting, the lower jaw 21 is forced to gradually shift in position in a three-dimensional manner by the mouthpiece, to thereby produce new axes X, Y and Z. In accordance with these new axes X, Y and Z, the projections 6, 7 are re-adjusted in length and also the processed surfaces $B_1$, $B_2$ of the supporting surfaces 10 are scraped to be adequately angled.

A series of operations comprising the check of the body axis C, the confirmation of the new axes X, Y and Z and the adjustment in length of the projections 6, 7, as well as in the inclination of the supporting surfaces 10 are repeatedly carried out, in order to bring the body axis C over time closer to the ideal body axis $C_0$. It is preferable that thereafter, the same adjustments are carried out about once every month.

The patient should preferably wear the thus adjusted mouthpiece 1 for a period of about 6 months to about 12 months. Though it is ideal to wear the mouthpiece 1 all day long, if it is difficult to do so, then the patient is prompted to wear it for about 12 hours a day. It should be noted, however, that the patient should wear the mouthpiece without fail during sleeping hours and during physical exercise. Due to this fitting, the groups of lower jaw supporting muscles of the both right and left sides gradually come to be substantially equal in length and thereby the patient's spine is straightened and his/her posture is corrected. Further, the muscles of both the right and left sides of the entire body gradually come to have and hold substantially equal length and strength and, as a result, indefinite complaints, function of the brain, athletic talents, physical capabilities, learning ability and the like are improved.

Figure 5B:
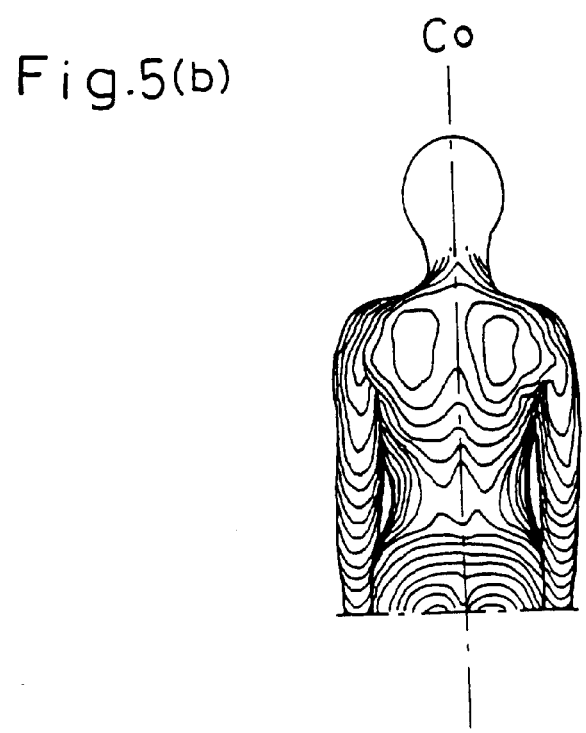

To this end, the patient having wore the mouthpiece 1 for about 1 month has the result that the body axis of the patient became approximate to the ideal body axis $C_0$, as shown in FIG. 5(b).

According to the mouthpiece 1 of this embodiment of the invention, since the projections 6, 7 are each formed into a conical shape that gradually becomes smaller toward the tip, the projections 6, 7 can be adjusted in length with ease and, hence, the bite raising quantity of the vertical occlusal height can be adjusted with ease. In addition, since the projections 6, 7 are relatively small in number and their tips are brought into nearly point contact with the supporting surfaces 10, areas of the supporting surfaces required for the formation of shearing drag surfaces can be reduced and, thus, the adjustment process can be facilitated.

Thus, the mouthpiece 1 of this embodiment of the invention can eliminate the need of grinding the shearing drag surfaces separately for each tooth, which is different from the prior art, and can save hours of labor or the requirement of a high degree of skill for the process.

In the embodiment illustrated above, the upper tooth row fitting groove 5 and the lower tooth row fitting groove 12 are formed by the process that after the teeth patterns of the row of teeth 20 on the upper jaw side and the row of teeth 23 on the lower jaw side are taken and then transferred to the upper piece 2 and the lower piece 3, both pieces are formed to have a size to snugly fit to the teeth by a fine grinding adjustment. The tooth row fitting grooves of the present invention are not limited to this configuration.

Figure 8:
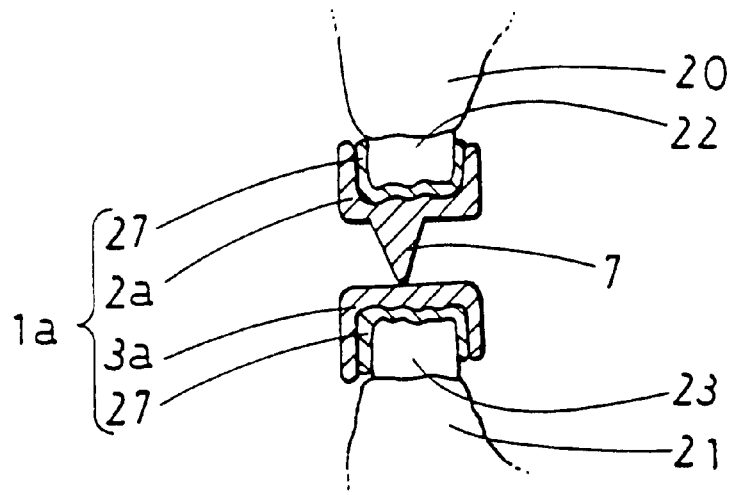
FIG. 8 is an illustration showing in section a mouthpiece according to another embodiment of the invention.

For example, as the mouthpiece 1a shown in FIG. 8, the tooth row fitting grooves of the upper piece 2a and the lower piece 3a may be formed to be slightly larger than the outlines of the rows of teeth, for a rough fit to the rows of teeth. In this mouthpiece 1a, the upper piece 2a is supported to the row of teeth 22 on the upper jaw side through soft lining material 27 filled in the upper tooth row fitting groove of the upper piece 2a. The lower piece 3a is also supported to the row of teeth 23 on the lower jaw side through the soft lining material 27.

Thus, according to the mouthpiece 1a, after the commercially available soft lining material 27 (which is sometimes called denture stabilizing material) is filled in the tooth row fitting grooves, both pieces are fitted to their respective rows of teeth. This can produce the result of saving hours of labor and cost for the highly precise processing of the tooth row fitting grooves.

Figure 9:
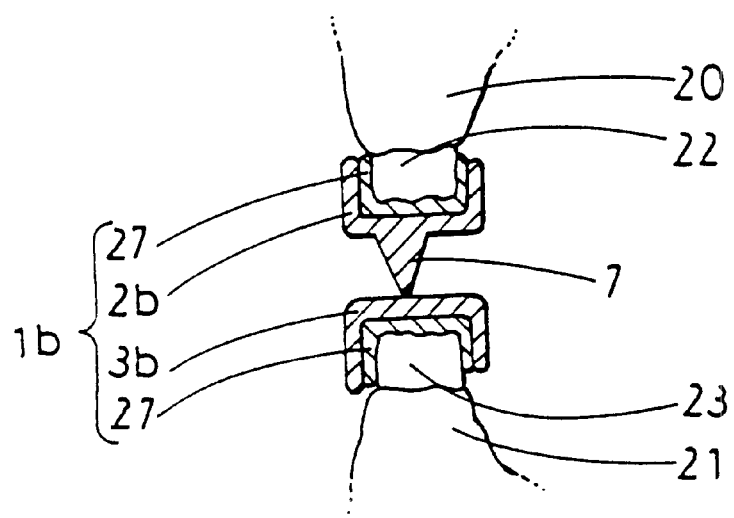
FIG. 9 is an illustration showing in section a mouthpiece according to still another embodiment of the invention.

Further, the mouthpiece 1b may comprise the upper piece 2b and the lower piece 3b having their respective tooth row fitting grooves which are formed into simple straight-sided grooves, as shown in FIG. 9. Also, in this mouthpiece 1b, the upper piece 2b and the lower piece 3b are fitted to the row of teeth 21 on the upper jaw side and the row of teeth 22 on the lower jaw side with ease and are held thereto through the soft lining material 27. For the dental clinic, there is only a need to grind the shearing drag surfaces at four locations thereof to contact with the projections 6, 7, for fitting adjustment, and there is no need to process the tooth row fitting grooves by grinding. Hence, this mouthpiece can provide the advantage of being useable immediately, thus saving hours of labor and cost for the process to a large extent. This may help a patient who suffers from indefinite complaints caused by poor occlusion but partly gives up on dental treatment because of the high costs of medical care.

Figure 10:
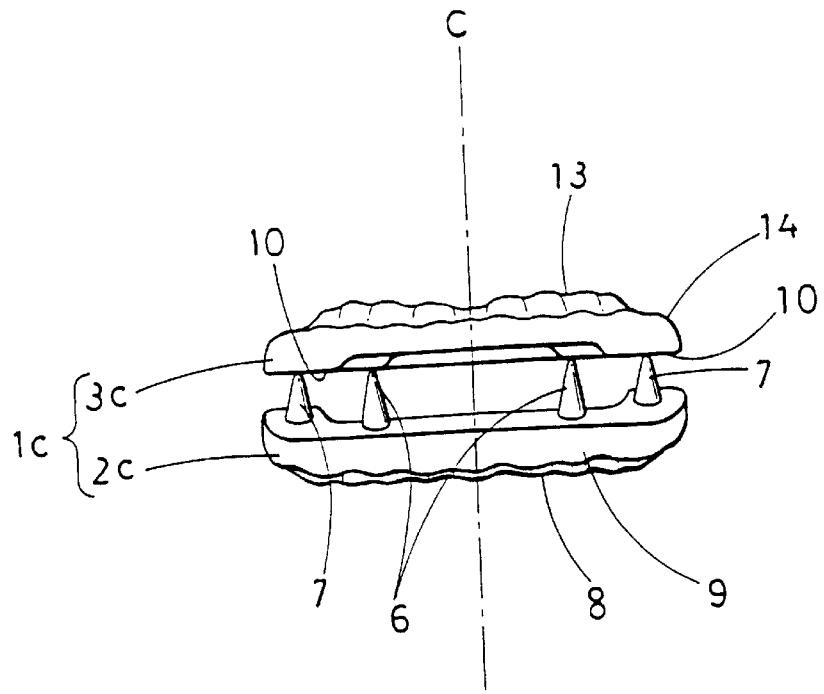
FIG. 10 is a front view of a mouthpiece according to a further embodiment of the invention.

The upper piece and the lower piece of the embodiments illustrated above may be modified to be replaced with each other, as shown in FIG. 10. Specifically, in the mouthpiece 1c, the lower piece 2c is provided with the upward projections 6, 6, 7, 7 and the upper piece 3c is provided with the supporting surfaces 10, 10 at a bottom thereof. This mouthpiece 1c can also provide the same effect as the mouthpieces 1–1b mentioned above.

Figure 11:
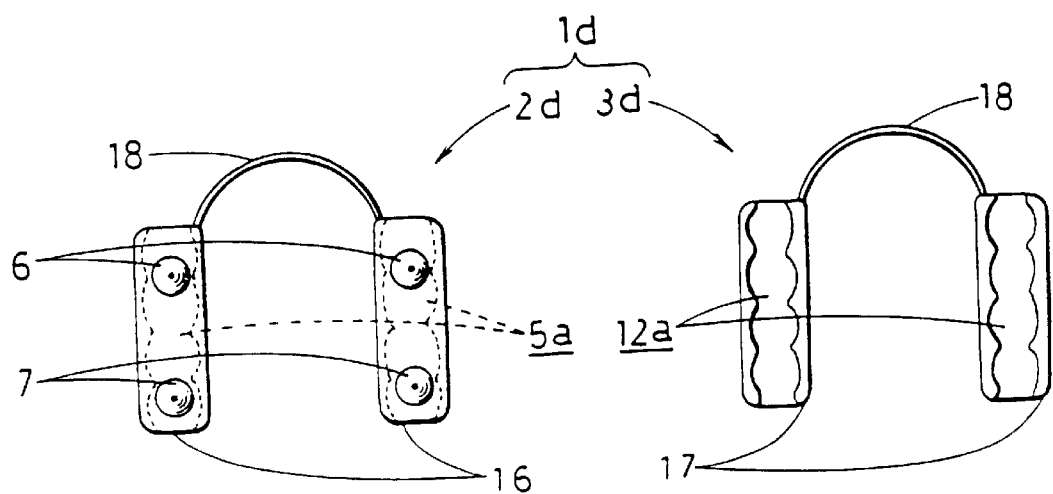
FIG. 11 is a bottom view showing a mouthpiece according to a still further embodiment of the invention.

While examples of the mouthpiece to be fitted to all teeth were shown in the embodiments illustrated above, the mouthpiece 1d may comprise an upper piece 2d comprising upper tooth row fitting pieces 16, 16 to be fitted to the premolars and molars only and a connecter 18 for connecting between the upper row fitting pieces 16, 16 and a lower piece 3d comprising lower tooth row fitting pieces 17, 17 to be fitted to the premolars and molars only and a connecter 18 for connecting between the lower row fitting pieces 17, 17, as shown in FIG. 11.

In this type of mouthpiece, the upper tooth row fitting groove 5a and the lower tooth row fitting groove 12a are also not limited to the ones formed in a tooth pattern and ground to snugly fit to the teeth, but may be formed into a rough groove form, for use in combination with the soft lining material 27 (See FIGS. 8 and 9).

Also, while examples of the mouthpiece 1–1d provided with the four projections were shown in the embodiments illustrated above, the present invention is not limited to this configuration. It is enough for the mouthpiece to have at least two projections. When an increased number of projections are provided on one of the two pieces, the corresponding number of shearing drag surfaces must be prepared on the opposing surface of the other piece. If fourteen projections are provided on the one piece, then the same number of shearing drag surfaces must be formed on the other piece, but, since spaces or openings are formed between the projections, the fitting process can be made with considerable ease. The projections of the invention are not limited to the conical configuration illustrated above. Any other configurations may be adopted for the projections, including, for example, column-shaped, elliptic-cylinder-shaped, rectangular-column-shaped, and pyramid-shaped.

Figure 12:
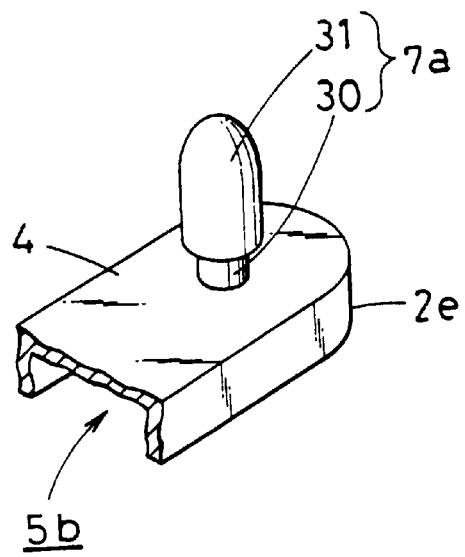
FIG. 12 is an outline view of a principal part of a projection of a variant.
Figure 13:
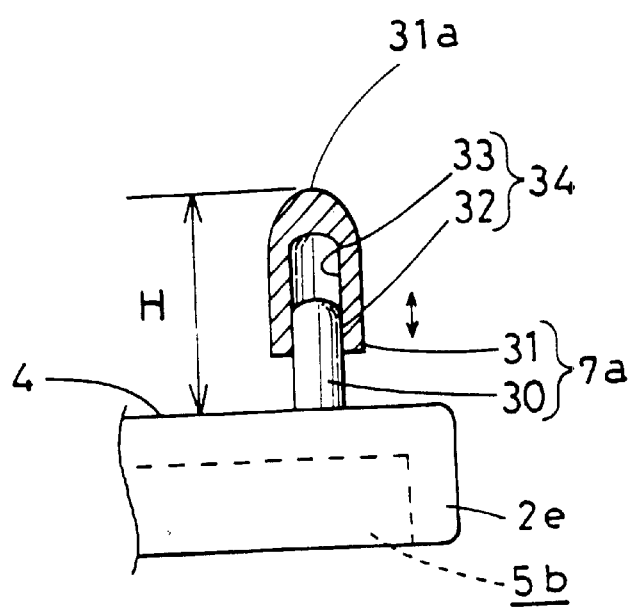
FIG. 13 is a partially sectioned view of the projection of the variant.

Referring now to FIGS. 12 and 13, there is shown another example of the projections. In FIGS. 12 and 13, the projections 7a of this mouthpiece each comprise a projecting piece 31 formed separately from the opposing surface 4 of the lower piece 2e and a projection height adjusting means 34 for guiding the projecting piece 31 toward the upper piece 3e to vary the height H of the projection from the opposing surface 4 to the tip 31a.

The projection height adjusting means 34 comprises a first sliding surface 33 formed by an inner surface of a vertical hole formed in the projecting piece 31 and a second sliding surface 32 formed by an outer surface of a pin 30 standing from the opposing surface 4. In detail, the first sliding surface 33 of the projecting piece 31 is so formed that the projecting piece 31 can slide over the second sliding surface 32 of the pin 30 toward the upper piece 3e (See FIGS. 14(a) and (b)).

Figure 14A:
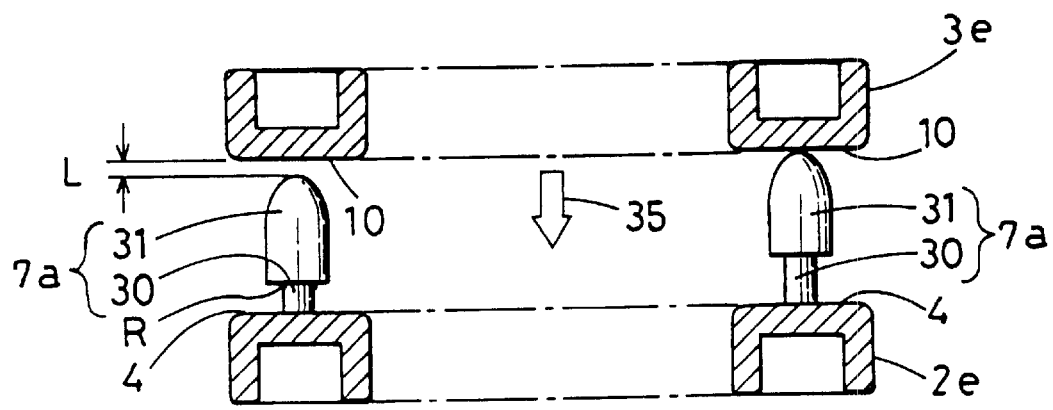
FIGS. 14(a) and (b) illustrate the way of adjustment in length of the projection of the variant, with FIG. 14(a) being an illustration showing the state in which one of the projections is in contact with the opposing surface but the other is not in contact with the same, and FIG. 14(b) being an illustration showing the state in which the both projections are in contact with their respective opposing surfaces.

When the projection 7a thus constructed is adjusted to an adequate length, one projecting piece 31 (the one depicted at the left side as viewed in the diagram) is first fixed to the pin 30 by adhesive R at a position corresponding to an adequate height of the projection, as shown in FIG. 14(a). The other projecting piece 31 (the one depicted at the right side as viewed in the diagram) is loosely fitted to the pin 30 so that it can freely slide vertically.

Then, when the upper piece 3e is moved close to the lower piece 2e (in the direction indicated by an arrow 35 in the diagram), the tip of the projecting piece 31 at the right side comes into abutment with the opposing surface 10 of the upper piece 3e, first. At this time, a clearance L is formed between the tip of the projecting piece 31 at the left side and the opposing surface 10 of the upper piece 3e.

Figure 14B:
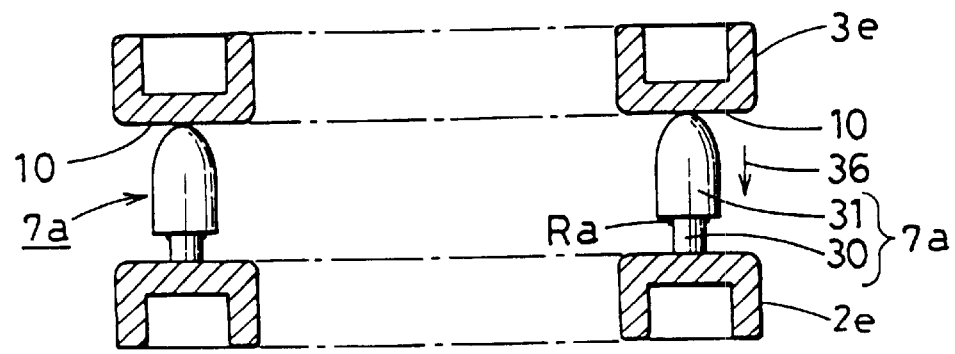

When the upper piece 3e is continuously moved further in the arrow 36 direction, as shown in FIG. 14(b), the projecting piece 31 at the right side is pressed down, while the first sliding surface 33 is slid over the second sliding surface 32, so that the pin 30 goes into the vertical hole of the projecting piece 31. Then, the tip of the projecting piece 31 at the left side is soon brought into abutment with the opposing surface 10 of the upper piece 3e.

At this point of time, the both projecting pieces 7a, 7a are brought into contact with the supporting surfaces 10, 10, whereat the projecting piece 31 at the right side is fixed to the pin 30 by means of adhesive Ra (which is an example of the projecting piece fixing means). This can eliminate the need of grinding the tip of the projections 6, 7, thus further facilitating the adjustment of the projection 7a to an adequate length.

Figure 15:
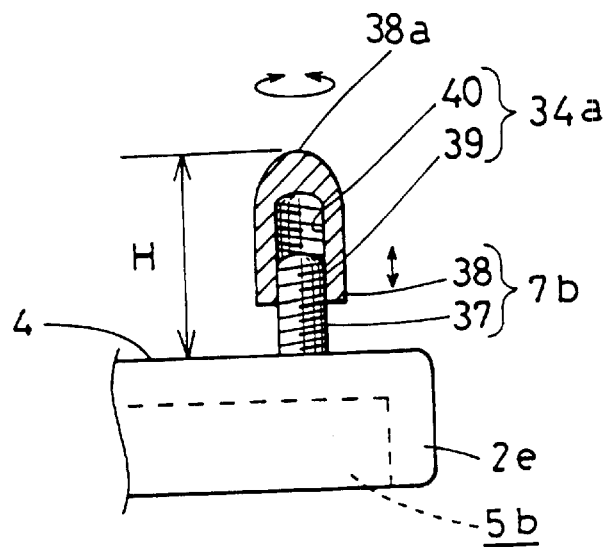
FIG. 15 is a partially sectioned view of a projection of another variant.

Referring further to FIG. 15, there is shown a principal part of another example of the lower piece. The projection 7b of FIG. 15 comprises a projecting piece 38 with a vertical hole having in its inner surface a first threaded portion 40 (female screw in this example) and a pin 37 standing from the opposing surface 4 side and having in its outer surface a second threaded portion 39 (male screw in this example) threadedly engageable with the first threaded portion 40.

According to this projection 7b, the height H of the projection from the opposing surface 4 to the tip 38a of the projecting piece 38 can be varied by screwing forward the projecting piece 38 with fingers. When the projection 7c is stopped screwing with the fingers, the projection 7c is fixed to the pin 37 on the opposing surface 4 side at that position. Thus, the projection height adjusting means 34a (one example of the projection height adjusting means and projecting piece fixing means as defined by the present invention) comprises the first threaded portion 40 and the second threaded portion 39. Thus, the combination of the first threaded portion 40 and the second threaded portion 39 can provide the combined function of the projection height adjusting means and the projecting piece fixing means of the present invention.

Figure 16:
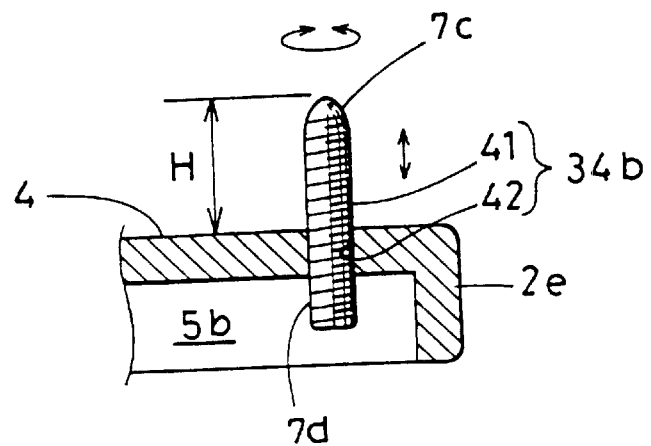
FIG. 16 is a partially sectioned view of a projection of still another variant.
Figure 17A:
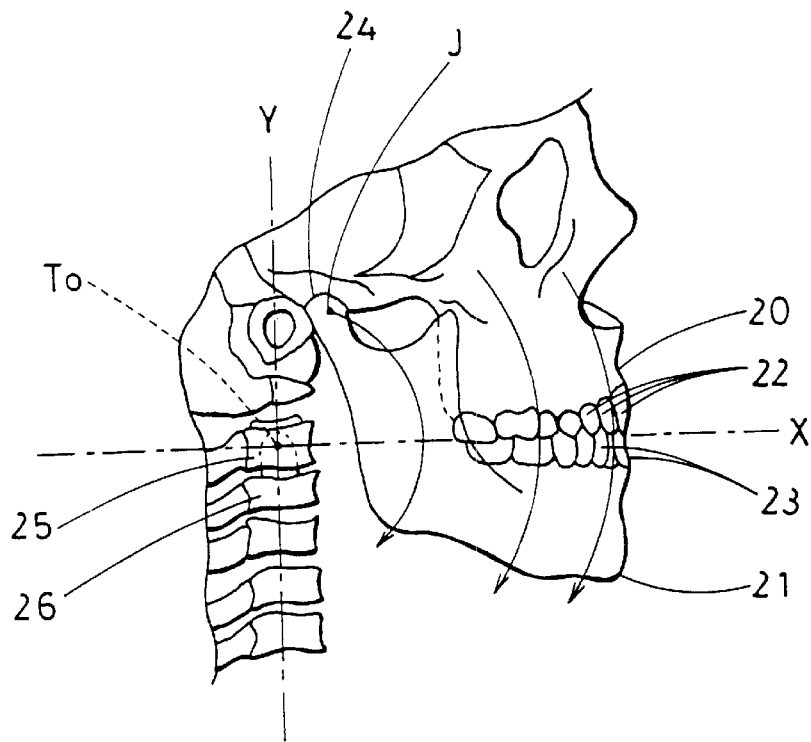
FIGS. 17(a) and (b) illustrate a general bone structure of and around the upper and lower jaws as viewed from the side elevation, with FIG. 17(a) being an illustration of the occlusion of the upper and lower rows of teeth, and FIG. 17(b) being an illustration of the state in which the lower jaw is opened.
Figure 17B:
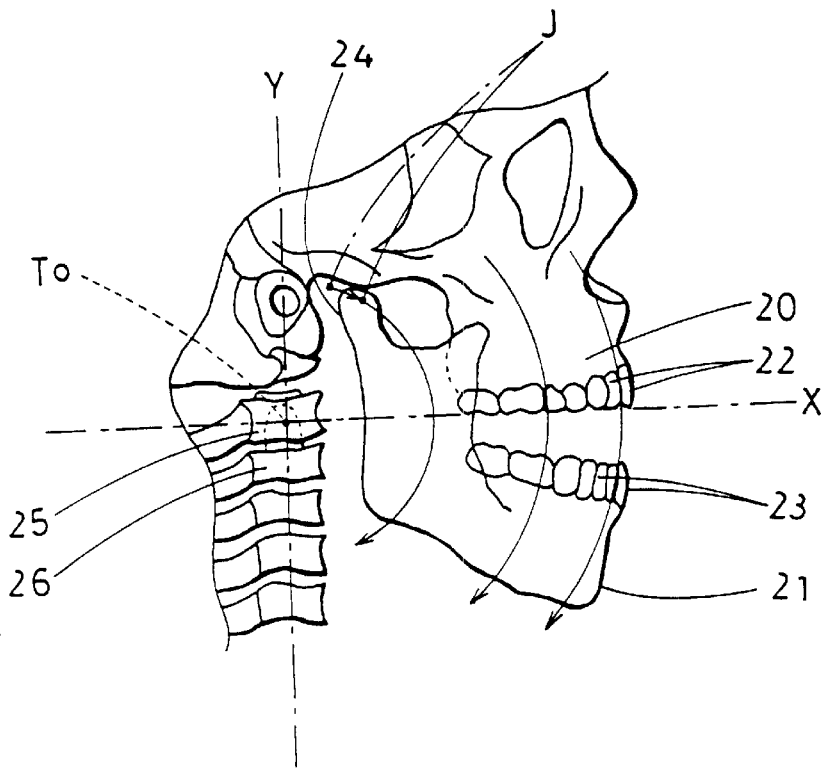

Referring now to FIG. 16, there is shown a principal part of still another example of the lower piece. The projection 7c of FIG. 16 is formed into a pin-like form and has a first threaded portion 41 of a male screw thereon. On the other hand, the lower piece 2e is provided, on its opposing surface 4, with a second threaded portion 42 of a female screw threadedly engageable with the first threaded portion 41.

In this example, the height H of the projection from the opposing surface 4 to the tip of the projection 7c can also be varied by screwing forward the projection 7c with fingers. When the screwing of the projection 7c is stopped, the projection 7c is fixed to the pin 37 on the opposing surface 4 side at that position. Thus, the projection height adjusting means 34b (another example of the projection height adjusting means and projecting piece fixing means as defined by the present invention) comprises the first threaded portion 41 and the second threaded portion 42.

After the adjustment of the height H of the projection, an end portion 7d of the projection 7c that is no longer required can be cut off easily with a snipper and the like.

CAPABILITIES OF EXPLOITATION IN INDUSTRY

According to the mouthpiece of the present invention, since the projections of the one piece are brought into abutment with the supporting surfaces of the other piece and are supported thereon, as mentioned above, the heights of the projections can be adjusted by filing off the projections with a dental file and the like or extending them. Thus, the bite raising quantity of the vertical occlusal height can be adjusted easily with just a little processing. Hence, dental treatment in the dental clinic can be simplified and thus finished in a matter of minutes. In addition, since the abutment condition between the projections and their related surfaces can be confirmed visibly through the openings between the projections, the adjustment of the height of the projections and in inclination of the shearing drag surfaces can be made with accuracy. Further, since the tips of the projections are brought into nearly point contact with the supporting surfaces, the patient can move his/her lower jaw with ease in the occlusal state, thus giving adequate play to the masseteric muscles.

In summary, the mouthpiece of the present invention can provide not only the result of equally stretching the right and left sides of the lower jaw supporting muscles by bite raising means, to correct one's posture, but also the results of being simplified in structure to facilitate an adjustment process for dental fitting and being provided at a significantly low price. Even for the mouthpiece designed for the patient of the occlusion corresponding to the type 2 occlusion or the type 3 occlusion, the adjustment of length of the projections and the adjustment in inclination of the shearing drag surfaces can be made easily, as is the mouthpiece easy for adjustment for the type 1 occlusion, by modifications of the opposing surfaces of the upper and lower pieces to be widened laterally and formed into level planes and of the projections being formed to extend along the vertical axis.

Also, the projections comprising the projecting pieces, the projection height adjusting means for varying the height of the projection and the projecting piece fixing means for fixing the projecting pieces to opposing surfaces can produce the result of adjusting the projections to adequate heights with a significantly simple operation.

Further, the projections adapted to be used in combination with the soft lining material can provide the advantage that the tooth row fitting grooves can be ground out to have a rough form somewhat larger than the row of teeth, thus eliminating the need for the highly precise processing of the tooth row fitting grooves. The adjustment of the vertical occlusal height can be made simply by grinding the projections a little bit, for fine adjustment, and adjusting an amount of soft lining material to be filled in the grooves. Thus, the mouthpiece of significantly low price and simple and easy constitution can be provided.

What is claimed is:

1. A mouthpiece comprising:
   an upper piece to be fitted to a row of teeth on an upper jaw side;
   a lower piece to be fitted to a row of teeth on a lower jaw side in a vertically confronting relation with said upper piece; and
   at least two projections projecting from one of a bottom surface of said upper piece and a top surface of said lower piece toward another of said upper piece and said lower piece without said at least two projections, wherein
   another surface of said bottom surface of said upper piece and said top surface of said lower piece without said at least two projections has a planar surface formed to support said at least two projections, be in slidable relation with said at least two projections in all directions along said planar surface, and be perpendicular to said at least two projections when said another surface and said at least two projections are in contact.

2. A mouthpiece according to claim 1, wherein each of said at least two projections comprises:

a projecting piece formed separately from said one of said bottom surface of said upper piece and said top surface of said lower piece;

projection height adjusting means for adjusting a height of projection of said projecting piece from said one of said bottom surface of said upper piece and said top surface of said lower piece toward said another of said upper piece and said lower piece; and projecting piece fixing means for fixing said projecting piece to said one of said bottom surface of said upper piece and said top surface of said lower piece at the height of projection set by said projection height adjusting means.

3. A mouthpiece according to claim 2, wherein said projection height adjusting means comprises a first sliding surface formed on said projecting piece and a second sliding surface formed on said one of said bottom surface of said upper piece and said top surface of said lower piece to slide along said first sliding surface of said projecting piece, so as to guide said projecting piece.

4. A mouthpiece according to claim 3, wherein a top surface of said upper piece has an upper tooth row fitting groove to be fitted to the row of teeth on the upper jaw side and a bottom surface of said lower piece has a lower tooth row fitting groove to be fitted to the row of teen on the upper jaw side.

5. A mouthpiece according to claim 4, further comprising a soft lining material being operable to fit said upper tooth row fitting groove and said lower tooth row fitting groove to the row of teeth on the upper jaw side and the row of teeth on the lower jaw side, respectively.

6. A mouthpiece according to claim 2, wherein said projection height adjusting means and said projecting piece fixing means comprise a first threaded portion provided on said projecting piece and a second threaded portion provided on said one of said bottom surface of said upper piece and said top surface of said lower piece to be threadedly engaged with said first threaded portion.

7. A mouthpiece according to claim 6, wherein a top surface of said upper piece has an upper tooth row fitting groove to be fitted to the row of teeth on the upper jaw side and a bottom surface of said lower piece has a lower tooth row fitting groove to be fitted to the row of teen on the upper jaw side.

8. A mouthpiece according to claim 7, further comprising a soft lining material being operable to fit said upper tooth row fitting groove and said lower tooth row fitting groove to the row of teeth on the upper jaw side and the row of teeth on the lower jaw side, respectively.

9. A mouthpiece according to claim 2, wherein a top surface of said upper piece has an upper tooth row fitting groove to be fitted to the row of teeth on the upper jaw side and a bottom surface of said lower piece has a lower tooth row fitting groove to be fitted to the row of teen on the upper jaw side.

10. A mouthpiece according to claim 9, further comprising a soft lining material being operable to fit said upper tooth row fitting groove and said lower tooth row fitting groove to the row of teeth on the upper jaw side and the row of teeth on the lower jaw side, respectively.

11. A mouthpiece according to claim 2, wherein said projection height adjusting assembly comprises a first sliding surface formed on said projecting piece and a second sliding surface formed on said one of said bottom surface of said upper piece and said top surface of said lower piece to slide along said first sliding surface of said projecting piece, so as to guide said projecting piece.

12. A mouthpiece according to claim 2, wherein said projection height adjusting assembly and said projecting piece fixing assembly comprise a first threaded portion provided on said projecting piece and a second threaded portion provided on said one of said bottom surface of said upper piece and said top surface of said lower piece to be threadedly engaged with said first threaded portion.

13. A mouthpiece according to claim 1, wherein a top surface of said upper piece has an upper tooth row fitting groove to be fitted to the row of teeth on the upper jaw side and a bottom surface of said lower piece has a lower tooth row fitting groove to be fitted to the row of teen on the upper jaw side.

14. A mouthpiece according to claim 13, further comprising a soft lining material being operable to fit said upper tooth row fitting groove and said lower tooth row fitting groove to the row of teeth on the upper jaw side and the row of teeth on the lower jaw side, respectively.

15. A mouthpiece according to claim 1, wherein each of said at least two projections comprises:

a projecting piece formed separately from said one of said bottom surface of said upper piece and said top surface of said lower piece;

projection height adjusting assembly being operable to adjust a height of projection of said projecting piece from said one of said bottom surface of said upper piece and said top surface of said lower piece toward said another of said upper piece and said lower piece; and projecting piece fixing assembly being operable to fix said projecting piece to said one of said bottom surface of said upper piece and said top surface of said lower piece at the height of projection set by said projection height adjusting apparatus.

* * * * *